(12) United States Patent
Grahek et al.

(10) Patent No.: US 8,044,086 B2
(45) Date of Patent: Oct. 25, 2011

(54) OXIDATIVE DEGRADATION PRODUCTS OF ATORVASTATIN CALCIUM

(75) Inventors: Rok Grahek, Kranj (SI); Darko Kocjan, Ljubljana (SI); Andrej Bastarda, Vrhnika (SI); Andrej Kocijan, Ljubljana (SI); Matjaz Kracun, Ljubljana (SI)

(73) Assignee: Lek Pharmaceuticals D.D., Ljubljana (SI)

( * ) Notice: Subject to any disclaimer, the term of this patent is extended or adjusted under 35 U.S.C. 154(b) by 606 days.

(21) Appl. No.: 11/632,608

(22) PCT Filed: Jul. 15, 2005

(86) PCT No.: PCT/EP2005/007739
§ 371 (c)(1),
(2), (4) Date: Mar. 9, 2007

(87) PCT Pub. No.: WO2006/008091
PCT Pub. Date: Jan. 26, 2006

(65) Prior Publication Data
US 2007/0208071 A1    Sep. 6, 2007

(30) Foreign Application Priority Data

Jul. 16, 2004 (SI) .................................. P200400209
Dec. 24, 2004 (SI) .................................. P200400348

(51) Int. Cl.
*A01N 43/38* (2006.01)
*A01N 43/36* (2006.01)

(52) U.S. Cl. ........................................ 514/412; 514/423

(58) Field of Classification Search .................... None
See application file for complete search history.

(56) References Cited

U.S. PATENT DOCUMENTS

| | | | |
|---|---|---|---|
| 5,003,080 A | 3/1991 | Butler et al. | |
| 5,097,045 A | 3/1992 | Butler et al. | |
| 5,103,024 A | 4/1992 | Millar et al. | |
| 5,124,482 A | 6/1992 | Butler et al. | |
| 5,149,837 A | 9/1992 | Butler et al. | |
| 5,155,251 A | 10/1992 | Butler et al. | |
| 5,216,174 A | 6/1993 | Butler et al. | |
| 5,245,047 A | 9/1993 | Butler et al. | |
| 5,248,793 A | 9/1993 | Millar et al. | |
| 5,273,995 A | 12/1993 | Roth et al. | |
| 5,280,126 A | 1/1994 | Butler et al. | |
| 5,342,952 A | 8/1994 | Butler et al. | |
| 5,397,792 A | 3/1995 | Butler et al. | |
| 5,686,104 A | 11/1997 | Mills et al. | |
| 2003/0114497 A1 | 6/2003 | Alani et al. | |

FOREIGN PATENT DOCUMENTS

| | | | |
|---|---|---|---|
| SI | 21302 A | | 4/2004 |
| WO | WO 01/45677 | * | 12/2000 |
| WO | 0132161 A2 | | 5/2001 |
| WO | 0137876 A2 | | 5/2001 |
| WO | 0158443 A1 | | 8/2001 |
| WO | WO03/011826 | | 2/2003 |
| WO | WO03/018547 | | 3/2003 |

OTHER PUBLICATIONS

Kerkhof; caplus an 2006:982493.*
Sebek et al., caplus an 2005:120702.*
Waterman, et al, 2002. "Stabilization of Pharmaceuticals to Oxidative Degradation" Pharmaceutical Development and Technology 7(1): 1-32.
Byrn, et al. Solid State Chemistry of Drugs, 2nd Edition. West Lafayette: SSCI, 1999. pp. 315-348.
Hurley: Photodecomposition of CI-981, an HMG-CoA reductase inhibitor Tetrehedron, Elsevier Science Publishers, Amsterdam, NL vol. 49, No. 10 Mar. 5, 1993, pp. 1979-1984, XP002363647 ISSN: 0040-4020.
International search report, 2004.

* cited by examiner

*Primary Examiner* — Sun Jae Loewe
(74) *Attorney, Agent, or Firm* — Merchant & Gould PC

(57) ABSTRACT

The present invention relates to oxidative degradation products of atorvastatin calcium and the process of the preparation thereof. The present invention also relates to atorvastatin calcium substantially free of oxidative degradation products and the pharmaceutical compositions containing such atorvastatin calcium.

3 Claims, No Drawings

OXIDATIVE DEGRADATION PRODUCTS OF ATORVASTATIN CALCIUM

This application is the National Stage of International Application No. PCT/EP/2005/007739, filed on Jul. 15, 2005, which claims benefit under 35 U.S.C. §119(a)-(d) or (f) or 365(b) of any foreign application(s) No. P200400348, filed on Dec. 24, 2004 and application No. P200400209, filed on Jul. 16, 2004, which contents are incorporated herein by reference in their entirety.

The present invention belongs to the field of organic chemistry and relates to oxidative degradation products of atorvastatin calcium and the processes for the preparation thereof. The present invention also relates to atorvastatin calcium substantially free of oxidative degradation products and pharmaceutical compositions containing such atorvastatin calcium.

The purity of the pharmaceutical active substances has always been considered as an essential factor in ensuring drug safety and quality. As it is well known in the art, the result of the many different complex steps in the production of a pharmaceutical active substance is not only the desired product but also impurities which are structurally closely related compounds. Additionally, many pharmaceutical active substances are sensitive to environmental influences such as for example temperature, pH, humidity, light, gases, oxygen, carbon dioxide, reactivity of the ambient medium during handling or storage. Such environmental influences may cause transformation of the pharmaceutically active compound into degradation products which are often less effective than the active compound. Apart from the lower efficacy, degradation products may also cause undesirable side effects thus negatively affecting the safe use of a medicament. Even a very low percent of impurities or degradation products present in the active substance may significantly impair drug safety. Therefore, it is very important that a pharmaceutical active substance is as pure as possible when administered; this means that the percentage of degradation products and impurities present in the pharmaceutical active substance should be minimal.

Moreover, the pharmaceutical excipients used in the pharmaceutical dosage form may also have an influence on the amount of degradation products and impurities present in the pharmaceutical active substances. Degradation products of the pharmaceutical excipients themselves may act as reactive sites triggering degradation reactions of the pharmaceutical active substances in a pharmaceutical dosage form.

The sensitivity of various pharmaceutical active substances to oxidative degradation is described by Waterman, K. C., et al., in "Stabilization of Pharmaceuticals to Oxidative Degradation", Pharmaceutical Development and Technology, 7(1), 2002, 1-32, and possible approaches to the stabilization of pharmaceutical active substances against oxidative degradation are also presented. The above-mentioned article suggests that the study of oxidative mechanism in solid pharmaceutical dosage forms is difficult and demanding, as it is indicated by few reports in said area, but however teaches that an active substance per se and more frequently an active substance in a pharmaceutical dosage form may oxidize. Byrn, S. R., et al. (Solid-State Chemistry of Drugs, $2^{nd}$ Ed., SSCI, West Lafayette, 1999) disclose that molecular oxygen from the atmosphere reacts with organic crystals and that said reactivity depends on the crystal form and morphology of the active substance, which determine permeability to oxygen and its solubility in the crystal lattice, respectively. In some examples the reactivity is shown to decrease with increased melting point indicating that higher crystalline lattice energy inhibits diffusion of oxygen.

For the prevention or reduction of the oxidation of an active substance in a pharmaceutical formulation different approaches have been used until now, such as, for example:

1. increasing the concentration of the active substance in a pharmaceutical formulation, in the case that oxidation is caused by the presence of peroxide and metallic impurities in excipients;
2. addition of chelating agents (e.g. citric acid, EDTA, fumaric acid and maleic acid) for removal of metallic impurities present in excipients;
3. use of high-purity pharmaceutical excipients;
4. use of alternative pharmaceutical excipients, or decrease in the amount of excipients in the pharmaceutical composition, particularly where the excipients are the cause of oxidation due to a peroxide impurity;
5. use of antioxidants which are capable of preventing or reducing the formation of peroxides in a pharmaceutical composition. However, such antioxidants do not reduce the level of the already present peroxides at the same time. Some suitable antioxidants have been described previously, including:
   chain terminators (as e.g. thiols and phenols);
   reducing agents which are more readily oxidized than an active substance and thus remove present oxygen (e.g. sulfites and ascorbic acid) wherein their combination may act synergistically (e.g. a combination of ascorbic palmitate and tocopherol);
   peroxide >>scavengers<< which degrade peroxides (e.g. $Fe^{2+}$) on the principle of Fenton's procedure. However, their use is limited because by this procedure a free hydroxyl radical may be formed which may further induce reactions of free radicals and thus degradation of an active substance;
   cyclodextrins which cover the site of an active substances subjected to oxidation (Waterman, K. C., et al., Stabilization of Pharmaceuticals to Oxidative Degradation, Pharmaceutical Development and Technology, 7(1), 2002, 1-32).

However, for individual active substances it is impossible to envisage optimal modes and few publications are available in the field (Waterman, K. C., et al., Stabilization of Pharmaceuticals to Oxidative Degradation, Pharmaceutical Development and Technology, 7(1), 2002, 1-32).

Atorvastatin calcium, which has the chemical name hemi-calcium salt of (R-(R*,R*))-2-(4-fluorophenyl)-β,δ-dihydroxy-5-(1-methylethyl)-3-phenyl-4((phenylamino)carbonyl)-1H-pyrol-1-heptanoic acid, is known as an inhibitor of 3-hydroxy-3-methylglutaryl-coenzyme A (HMG-CoA) reductase. It was described first time in U.S. Pat. No. 5,273,995. Processes for the preparation of atorvastatin calcium and key intermediates thereof are described in U.S. Pat. Nos. 5,003,080; 5,097,045; 5,103,024; 5,124,482; 5,149,837; 5,155,251; 5,216,174; 5,245,047; 5,248,793; 5,280,126; 5,342,952; and 5,397,792.

HMG-CoA reductase inhibitors are known to be pharmaceutically active substances which are sensitive to the pH of the environment, humidity, light, temperature, carbon dioxide and oxygen. They are known as effective therapeutically active substances for the treatment of dyslipidemias and cardiovascular diseases, selected from the group consisting of dyslipidemia, hyperlipidemia, hypercholesterolemia, atherosclerosis, arteriosclerosis, coronary artery diseases, coronary heart disease and the like, associated with the metabolism of lipids and cholesterol. The mechanism of action of statin compounds is by the inhibition of the biosynthesis of cholesterol and other sterols in the liver of humans or animals. They are competitive inhibitors of HMG-CoA reductase or 3-hydroxy-3-methyl-glutaryl-coenzyme A reductase, an enzyme which catalyses the conversion of HMG-CoA to mevalonate in the liver of humans or animals, which is an important step in the biosynthesis of cholesterol in the liver. Recent studies indicate that, in addition to the above-mentioned therapeutic effects, statins also have other therapeutic effects and, accordingly, they are useful in the treatment of diseases, abnormal conditions and disorders which are selected from the group consisting of vascular disorders, inflammatory disease, allergic disease, neurodegenerative disease, malignant disease, viral disease (WO 0158443), abnormal bone states, (WO 0137876), amyloid-β precursor protein processing disorders such as Alzheimer's disease or Down's Syndrome (WO 0132161).

To date next to nothing has been published on how to avoid the presence of oxidation products in atorvastatin substance, and the degradation products of atorvastatin calcium have not previously been identified. The prevention of oxidation of atorvastatin calcium by means of carrying out the preparation process in an inert atmosphere, and by packaging in suitable packaging under an inert atmosphere was described in the Slovenian patent application Sl P-200200244. The structure of one degradation product of atorvastatin calcium having the chemical name: 3-(4-Fluoro-benzoyl)-2-isobutyryl-3-phenyl-oxirane-2-carboxylic acid phenylamide, and its preparation by photodecomposition was described in the article Hurley, T. R. et al., Tetrahedron 49, 1993, 1979-1984.

In view of the importance of obtaining an active substance with a high level of purity there exists a need for the characterization of each impurity or degradation product present in the active substance and/or pharmaceutical composition. The characterization of each impurity or degradation product present in an active substance or pharmaceutical composition is particularly important in respect of those active substances for which the response factor of an impurity and/or degradation product for a specified analytical method (e.g. HPLC) varies from the response factor of the active substance. Namely, in such cases it can happen that the active substance is declared as pharmaceutically acceptable according to regulatory requirements although the real level of impurities or degradation products is in fact outside the permitted values.

The present invention meets a need in the art for obtaining atorvastatin calcium product in a highly pure, form, having a low content of oxidative degradation products, by a technologically simple manner and at a high yield, by characterization of three oxidative degradation products present in atorvastatin calcium and/or pharmaceutical compositions thereof.

One object of the present invention relates to novel compounds, which are oxidative degradation products of atorvastatin calcium, having the following chemical formulae and chemical names:

a) compound with formula I

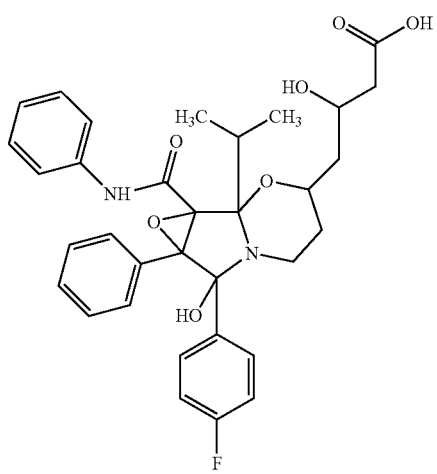

and chemical name
4-[6-(4-Fluoro-phenyl)-6-hydroxy-1b-isopropyl-6a-phenyl-1a-phenylcarbamoyl-hexahydro-1,2-dioxa-5a-aza-cyclopropa[a]inden-3-yl]-3-(R)-hydroxy-butyric acid (from hereon referred to as ATV-cycloIP);

b) compound with formula II

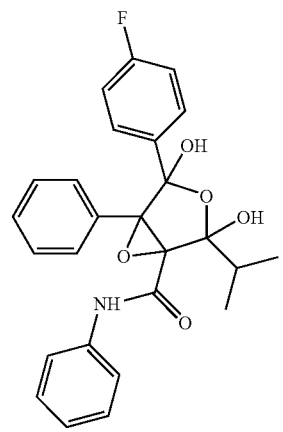

and chemical name
4-(4-Fluoro-phenyl)-2,4-dihydroxy-2-isopropyl-5-phenyl-3,6-dioxa-bicyclo[3.1.0]hexane-1-carboxylic acid phenylamide (from hereon referred to as ATV-epoxy furan);

c) compound with formula III

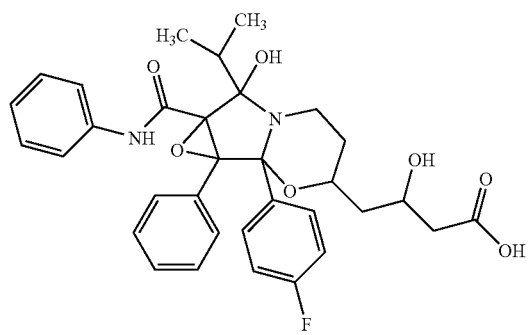

and chemical name 4-[1b-(4-Fluoro-phenyl)-6-hydroxy-6-isopropyl-1a-phenyl-6a-phenylcarbamoyl-hexahydro-1,2- dioxa-5a-aza-cyclopropa[a]inden-3-yl]-3-(R)-hydroxy-butyric acid (from hereon referred to as ATV-cycloFP).

The oxidative degradation product of atorvastatin calcium described in the article of Hurley, T. R. et al., Tetrahedron 49, 1993, 1979-1984 has the following chemical formula IV and chemical name:
3-(4-Fluoro-benzoyl)-2-isobutyryl-3-phenyl-oxirane-2-carboxylic acid phenylamide (from hereon referred to as ATV-epoxy dion).

The oxidative degradation of atorvastatin calcium may be represented by the following scheme:

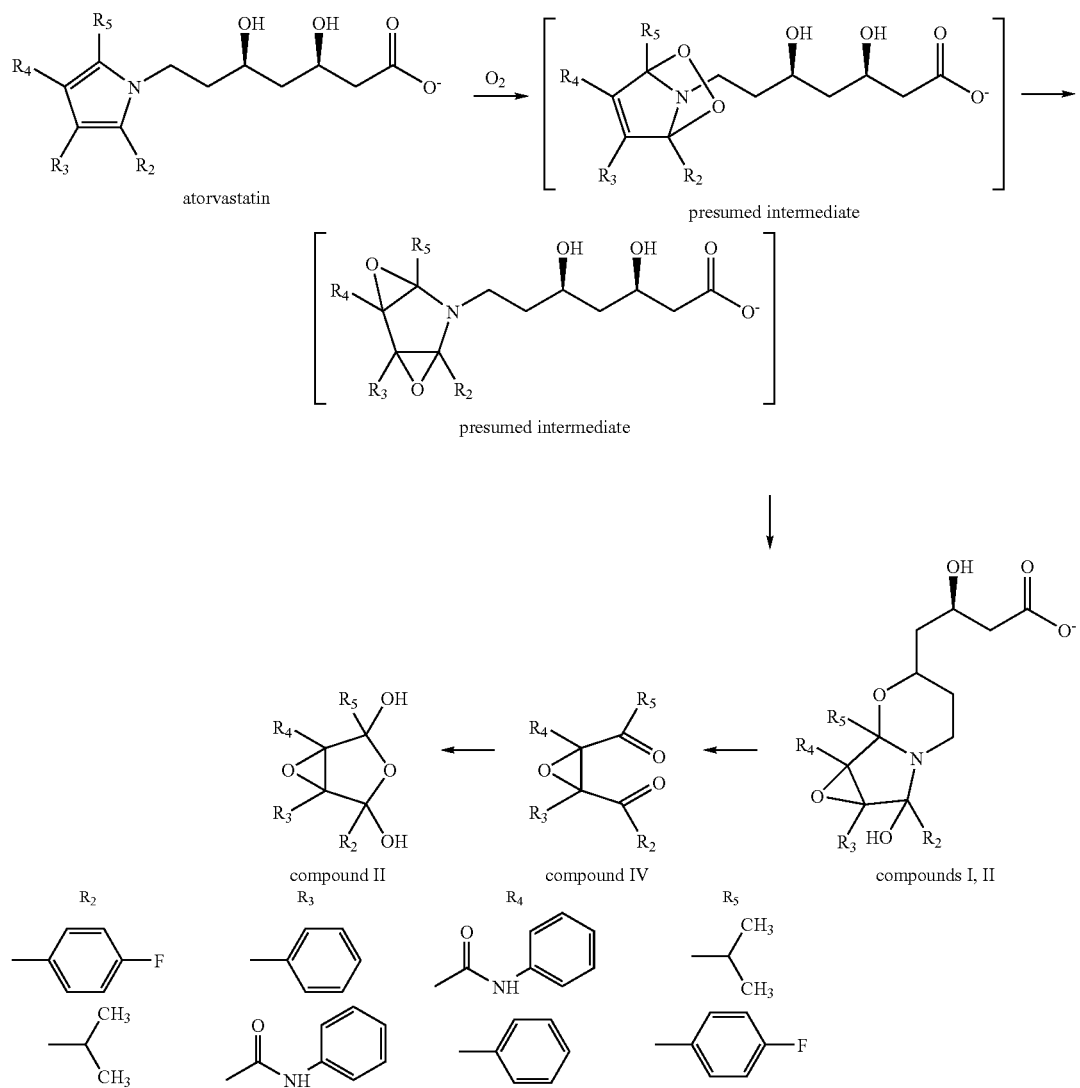

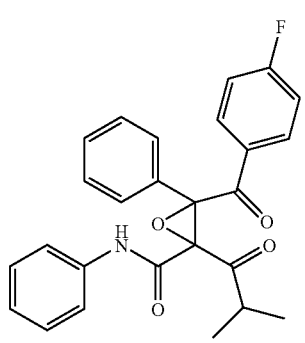

formula IV

The compounds with formula I, II, III and IV according to the present invention are present in atorvastatin calcium substance as oxidative degradation products, accordingly, it is very important that their amount should be minimized and that they should be detectable only in a very small amount. As impurities they present a risk of being toxic or otherwise harmful to the patient. For these reasons it is essential that their presence in the substance should be minimized. On the other hand it is very important that the level of these impurities is monitored accurately, accordingly their content should be determined correctly and exactly, e.g. by using standards (compound with known chemical structure and known assay) for quantitative determination.

The present invention also relates to novel processes for the preparation of compounds having the formula I, II, III and IV according to the present invention.

The novel compounds according to the present invention may be prepared by oxidation of solid atorvastatin in the form of a salt (for example as a calcium, sodium, potassium, magnesium, or ammonium salt) in an air or oxygen atmosphere at an elevated temperature, e.g. from 40 to 90° C. The reaction may last from 1 to several days. The oxidation may be performed in a solution of the atorvastatin salt in water and/or an organic solvent and/or mixtures of solvents, such as for example acetonitrile, methanol, ethanol, propanol, dichloromethane or methylene chloride; with the addition of hydrogen peroxide or by blowing air or oxygen through the solution at the temperature of about 40 to 90° C. The solid atorvastatin salt may be prepared by any known process.

The novel compounds according to the present invention may also be prepared by photo-oxidation of atorvastatin in the form of a salt (e.g. as a calcium, sodium, potassium, magnesium, ammonium salt) by exposing a solution of the atorvastatin salt to sunlight or artificial sunlight. The atorvastatin salt may be prepared by any known process.

The novel compounds according to the present invention prepared by the processes as described above may be isolated by preparative normal phase or reverse phase chromatography.

In preparative normal phase chromatography silica gel or silica-based bonded phases for example aminopropyl, cyanopropyl, diol, or nitrophenyl bonded stationary phases may be used. The mobile phase comprises a mixture of a polar modifier alcohol, for example methanol, ethanol, propanol or acetonitrile, and of a non-polar solvent as for example hexane, dichloromethane, methylcyclohexane, or a combination of more than two solvents listed above.

In preparative reverse phase chromatography octadecylsylan or octylsilan bonded on silica gel may be used. The mobile phase comprises a mixture of water with an organic or inorganic buffer in the concentration range from 5 mM to 100 mM and the pH range from 2 to 8, together with one or more organic modifiers selected from alcohols, such as for example methanol, ethanol and propanol, or acetonitrile.

One or more chromatographic steps may be used during the isolation of novel compounds according to the present invention. The solvents used in chromatographic steps may be removed by evaporation and/or by freeze drying.

The novel compounds according to the present invention prepared and isolated by the methods as described above were structurally characterized by Mass Spectrometry and Nuclear Magnetic Resonance spectroscopy in order to determine the chemical structure of the said novel compounds. The methods of characterization and their results are presented in the examples described below.

During the development work on preparing stable atorvastatin calcium compositions it has been found that atorvastatin calcium degrades when it comes into contact with air or more precisely with oxygen. Surprisingly the use of different antioxidants such as for example buthylated hydroxyanisole, buthylated hydroxytoluene, fumaric acid, propyl galate, sodium sulfite, sodium meta bisulfite, sodium ascorbate did not prevent or diminish the formation of the oxidative degradation products. Surprisingly, it has been found that by lowering the content of oxygen in the surrounding atmosphere of atorvastatin calcium or a pharmaceutical composition comprising atorvastatin calcium the formation of the oxidative degradation products in atorvastatin calcium may be significantly reduced. The observed reduction in oxidative degradation products was linearly proportional to the lowering of the oxygen content in the surrounding atmosphere. This lowering of the oxygen content may be performed by substitution of oxygen with an inert gas, for example nitrogen or argon, or by lowering the atmospheric pressure surrounding the atorvastatin calcium.

Besides carrying out the process of the preparation of atorvastatin calcium in an inert atmosphere and storing it in an inert atmosphere it is very important to monitor the amount of oxidative degradation products present in atorvastatin calcium substance and in the pharmaceutical composition comprising thereof. For determining the amount of undesired compounds it is necessary to provide standards of these compounds (this means the compounds with known chemical structure and assay) to be able to perform the exact quantitative analysis. This is of specific importance in cases where the response factor in e.g. HPLC analysis of impurity and/or degradation product is different in comparison to the response factor of the active substance. HPLC analysis is normally used for impurity determination in pharmaceutically active substances and pharmaceutical compositions.

Surprisingly, it has been found that some of the compounds present in atorvastatin calcium substance exhibit different response factor in comparison to atorvastatin calcium itself when HPLC analysis at 250 nm is performed. Namely, the novel compound according to the present invention with formula I exhibits 0.41 response factor, the novel compound according to the present invention with formula II exhibits 0.72 response factor, the novel compound according to the present invention with formula III exhibits 0.48 response factor and the compound with formula IV exhibits 1.20 response factor in comparison to atorvastatin calcium itself.

The content of impurities in an active substance and/or pharmaceutical composition is an important factor for the safety of the drug, therefore the content of impurities should be minimized. This is especially crucial for degradation products because their content in the drug rises during the shelf life of the drug.

A further object of the present invention is the provision of atorvastatin calcium substantially free of oxidative degradation products and pharmaceutical compositions containing said atorvastatin calcium and at least one pharmaceutically acceptable excipient.

The present invention provides substantially pure atorvastatin calcium which comprises less than about 0.29 weight % oxidative degradation products.

The present invention provides substantially pure atorvastatin calcium which comprises less than about 0.09 weight % ATV-cycloIP.

The present invention provides substantially pure atorvastatin calcium which comprises less than about 0.05 weight % ATV-epoxy furan.

The present invention provides substantially pure atorvastatin calcium which comprises less than about 0.09 weight % ATV-cycloFP.

The present invention provides substantially pure atorvastatin calcium which comprises less than about 0.06 weight % ATV-epoxy dione.

The Table 1 below shows the amount of each oxidative degradation product present in atorvastatin calcium exposed to various atmospheric conditions underwhich the process for the preparation was carried out.

When atorvastatin calcium is prepared or stored in an air atmosphere at the room temperature oxidative degradation products are formed. This can be avoided when atorvastatin calcium is stored in a nitrogen atmosphere.

TABLE 1

The content of oxidative degradation products in atorvastatin calcium when atorvastatin calcium is prepared in air and in a nitrogen atmosphere. The analysis was performed using the response factor 1.00 for all substances.

| Production atmosphere | Content of ATV-cycloIP in % | Content of ATV-epoxy furane in % | Content of ATV-cycloFP in % | Content of ATV-epoxy dion in % |
|---|---|---|---|---|
| air | 0.088 | 0.066 | 0.093 | 0.069 |
| nitrogen | 0.013 | 0.011 | 0.018 | 0.016 |

TABLE 2

The content of oxidative degradation products in atorvastatin calcium prepared in air or in a nitrogen atmosphere. The analysis was performed using the response factors 0.41 for ATV-cycloIP, 0.72 for ATV-epoxy furan, 0.48 for ATV-cycloFP and 1.20 for ATV - epoxy dion.

| Production atmosphere | Content of ATV-cycloIP in % | Content of ATV-epoxy furane in % | Content of ATV-cycloFP in % | Content of ATV-epoxy dion in % |
|---|---|---|---|---|
| air | 0.215 | 0.093 | 0.193 | 0.058 |
| nitrogen | 0.032 | 0.016 | 0.038 | 0.013 |

The comparison between the Table 1 considering response factor for oxidative degradation products as 1.00 and the Table 2 considering the determined response factors show the essential difference in content values. When standards of the impurities are not used and the response factor 1.00 is applied, the determined values of oxidative degradation products in atorvastatin calcium prepared in air or in a nitrogen atmosphere are below the values determined by using the exact response factor. Also the content of the oxidative degradation products determined using the response factor 1.00 may be below the threshold of 0.10% above which the impurities should be identified according to the generally accepted pharmaceutical regulations. Further, due to the fact having a response factor greater than 1.00, the content of ATV-epoxy dion as determined using the response factor 1.00 is above the value determined by using the exact response factor.

All further analyses were performed using the response factors 0.41 for ATV-cycloIP, 0.72 for ATV-epoxy furan, 0.48 for ATV-cycloFP and 1.20 for ATV-epoxy dion.

TABLE 3

The content of oxidative degradation products in atorvastatin calcium stored in air or in a nitrogen atmosphere for 24 months at room temperature (for example 25° C.).

| Storing atmosphere | Content of ATV-cycloIP in % | Content of ATV-epoxy furan in % | Content of ATV-cycloFP in % | Content of ATV-epoxy dion in % |
|---|---|---|---|---|
| air | 0.856 | 0.636 | 0.905 | 0.741 |
| nitrogen | 0.094 | 0.052 | 0.088 | 0.063 |

The present invention provides a pharmaceutical composition comprising substantially pure atorvastatin calcium which comprises less than about 0.6 weight % oxidative degradation products and at least one pharmaceutically acceptable excipient.

The present invention provides a pharmaceutical composition comprising substantially pure atorvastatin calcium which comprises less than about 0.2 weight % ATV-cycloIP and at least one pharmaceutically acceptable excipient.

The present invention provides a pharmaceutical composition comprising substantially pure atorvastatin calcium which comprises less than about 0.1 weight % ATV-epoxy furan and at least one pharmaceutically acceptable excipient.

The present invention provides a pharmaceutical composition comprising substantially pure atorvastatin calcium which comprises less than about 0.2 weight % ATV-cyclo FP and at least one pharmaceutically acceptable excipient.

The present invention provides a pharmaceutical composition comprising substantially pure atorvastatin calcium which comprises less than about 0.1 weight % ATV-epoxy dion and at least one pharmaceutically acceptable excipient.

TABLE 4

The content of oxidative degradation products in atorvastatin calcium formulated into pharmaceutical formulation in the form of tablets stored in air or in a nitrogen atmosphere in Al/Al blisters for 24 months at room temperature (for example 25° C.).

| Storing atmosphere | Content of ATV-cycloIP in% | Content of ATV-epoxy furan in % | Content of ATV-cycloFP in % | Content of ATV-epoxy dion in % |
|---|---|---|---|---|
| air | 1.75 | 0.61 | 1.23 | 0.65 |
| nitrogen | 0.18 | 0.08 | 0.17 | 0.09 |

The results shown in Tables 3 and 4 show that when atorvastatin calcium or a pharmaceutical formulation containing atorvastatin calcium in the form of tablets are stored in an air atmosphere at the room temperature for 24 months oxidative degradation products dramatically increase. This can be avoided when atorvastatin calcium is stored in a nitrogen atmosphere.

The pharmaceutical composition according to the present invention may be administered to a mammal in a dosage form. The dosage form contains substantially pure atorvastatin calcium according to the present invention and at least one pharmaceutically acceptable excipient selected from the group consisting of diluents, binders, disintegrants, lubricants, glidants, flavorings, sweeteners, preservatives, dyes and other excipients used in preparing pharmaceutical composition. The pharmaceutical composition according to the present invention can be any dosage form that is used in pharmaceutical industry such as, for example, tablets, orally dispersible formulations, capsules, pellets, granulate, etc. Nitrogen or argon can be used as the inert gas for maintenance of an inert atmosphere. The pharmaceutical composition can be stored in an inert atmosphere in an Al/Al blister, Al-polychloro-3-fluoroethylene homopolymer/PVC laminate blister or bottles.

The pharmaceutical composition according to the present invention are useful in the treatment of hypercholesterolemia and hyperlipidemia.

The present invention is illustrated but in no way limited by the following examples:

EXAMPLE 1

Preparation and Isolation of ATV-cycloIP, ATV-Epoxy Furan, ATV-cycloFP and ATV-Epoxy Dion Compounds 5 grams of atorvastatin calcium was stored in a 200 ml airtight container in oxygen atmosphere for 30 days at 80° C.

The thus prepared sample was dissolved in 50% acetonitrile/water (vol/vol) and subjected to preparative chromatography.

Preparative chromatography: Isolation of oxidative degradation products was carried out on a reverse-phase chromatography. Two chromatographic separations with different mobile phases were necessary to obtain pure compounds.

The first separation was carried out on a preparative HPLC chromatograph equipped with Luna prep C18(2) 10 μm column (200 mm×50 mm) and UV detector set at 250 nm. The two mobile phases solvents, A and B, were 10 mM ammonium acetate pH 4.5 and 95% acetonitrile/5% tetrahydrofuran (vol/vol), respectively. The flow rate was 140 ml/min. The following gradient profile was used:

| Time (min:sec) | % B |
|---|---|
| 0 | 5 |
| 0:22 | 5 |
| 0:25 | 30 |
| 14 | 75 |
| 14:10 | 90 |
| 15 | 90 |
| 15:10 | 5 |

Four fractions were collected; the pH of fractions one and two was adjusted to 8-9 with 1M potassium hydroxide, the pH of fraction three and four was adjusted to 2-3 with 1M hydrochloric acid. The fractions were evaporated under reduced pressure. The water bath temperature was kept under 30° C. and condenser was cooled with water at 0° C.

All four fractions were additionally purified to obtain pure substances.

Purification of fraction one: The conditions for the purification of the fraction one were the same as those at the first separation, except the mobile phase A was 10 mM ammonium hydrogen carbonate. The following gradient profile was used:

| Time (min:sec) | % B |
|---|---|
| 0 | 10 |
| 0:17 | 10 |
| 0:22 | 36 |
| 7 | 36 |
| 7:10 | 90 |
| 8 | 90 |
| 8:10 | 10 |

One fraction was collected; the pH was adjusted to 8-9 with 1M potassium hydroxide. The fraction was evaporated under reduced pressure in the same manner as after the first chromatographic separation.

170 mg of pure ATV-cycloIP (4-[6-(4-Fluoro-phenyl)-6-hydroxy-1b-isopropyl-6a-phenyl-1a-phenylcarbamoyl-hexahydro-1,2-dioxa-5a-aza-cyclopropa[a]inden-3-yl]-3-(R)-hydroxy-butyric acid) compound was isolated from the concentrated fraction by freeze drying. The chromatographic purity was 97.2%.

Purification of Fraction Two:

Chromatographic conditions for the purification of the fraction two were the same as those for the first separation with the exception that. the mobile phase A solvent was 70% 10 mM phosphate buffer pH7.0/25% acetonitrile/5% tetrahydrofuran (vol/vol/vol) and the following gradient profile was used:

| Time (min:sec) | % B |
|---|---|
| 0 | 0 |
| 1:55 | 0 |
| 2 | 15 |
| 11:30 | 15 |
| 14:20 | 35 |
| 14:45 | 85 |
| 17:30 | 85 |

One fraction was collected and evaporated under reduced pressure. The concentrated fraction was loaded on a reverse phase column, buffer salts were washed out with water and the ATV-cycloFP compound was eluted from the column with 80% acetonitrile, 20% water (vol/vol).

185 mg of pure ATV-cycloFP (4-[1b-(4-Fluoro-phenyl)-6-hydroxy-6-isopropyl-1a-phenyl-6a-phenylcarbamoyl-hexahydro-1,2-dioxa-5a-aza-cyclopropa[a]inden-3-yl]3-(R)-hydroxy-butyric acid) compound was isolated from the concentrated fraction by freeze-drying. The chromatographic purity was 97.5%.

Purification of Fraction Three:

Chromatographic conditions for the purification of the fraction three were the same as those for the separation, except that the mobile phase A solvent was 5 mM hydrochloric acid and the following gradient profile was used:

| Time (min:sec) | % B |
|---|---|
| 0 | 20 |
| 0:17 | 20 |
| 0:22 | 72 |
| 7 | 72 |
| 7:10 | 20 |

One fraction was collected and evaporated under reduced pressure in the same manner as the fractions from the first separation.

205 mg of pure ATV-epoxy furan (4-(4-Fluoro-phenyl)-2,4-dihydroxy-2-isopropyl-5-phenyl-3,6-dioxa-bicyclo[3.1.0]hexane-1-carboxylic acid phenylamide) compound was isolated from the concentrated fraction by freeze-drying. The chromatographic purity was 93.6%.

Purification of Fraction Four:

Chromatographic conditions for the purification of the fraction four were the same as those for the purification of the fraction three, except that the following gradient profile was used:

| Time (min:sec) | % B |
|---|---|
| 0 | 20 |
| 0:17 | 20 |
| 0:22 | 75 |
| 7 | 75 |
| 7:10 | 20 |

One fraction was collected and evaporated under reduced pressure in the same manner as the fractions from the first separation.

50 mg of pure ATV-epoxy dion (3-(4-Fluoro-benzoyl)-2-isobutyryl-3-phenyl-oxirane-2-carboxylic acid phenylamide) compound was isolated from the concentrated fraction by freeze-drying. The chromatographic purity was 96.2%.

Structural Elucidation of Compound ATV-cycloIP:

Mass Spectrometry:

Conditions:

High-resolution mass spectra were obtained using a quadrupole time-of-flight mass spectrometer Micromass Q TOF Ultima Global. Electrospray ionisation was used. The source temperature was set to 100° C., desolvation temperature to 200° C., cone gas 0 L/h and desolvation gas 200 L/h. W geometry of TOF analyser was employed. The instrument was calibrated using Na-formate clusters. The sample was dissolved in 50% solution of 5 mM ammonium acetate/acetonitrile (vol/vol), and infused to mass spectrometer with constant flow of 10 μl/min. The concentration of the sample solution was 0.05 mg/ml.

Atorvastatin calcium salt was used as the internal standard for high-resolution measurements. A concentration of 0.01 mg/ml of the internal standard was added to a sample solution.

Protonated molecular ion 591.2507 m/z was observed. The calculated elemental composition was $C_{33}H_{36}N_2O_7F$. The deviation between the calculated and the measured mass was 0.5 mDa. In comparison with atorvastatin calcium the compound ATV-cycloIP shows two additional oxygen atoms in its chemical structure.

Nuclear Magnetic Resonance Spectroscopy:

Conditions:

$^1H$ and $^{13}C$ measurements were performed on a 300 MHz Varian instrument INOVA or UNITY 300. The INOVA instrument was equipped with a 5 mm inverse detect pulsed field gradient probe. $^1H$ and $^{13}C$ spectra were obtained by the measurements at the room temperature.

Samples were dissolved in methanol, chloroform or mixture of methanol and chloroform 2:1.

Chemical shifts in ppm are assigned with reference to the residual signal of the solvent.

| Solvent: | $CD_3OD$ ($^1H$ and $^{13}C$ measurements) | |
|---|---|---|

Structure:

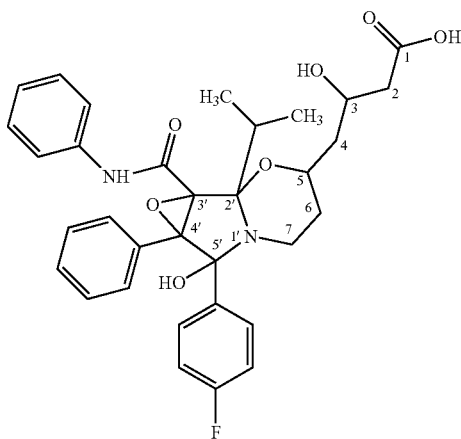

$^1H$ NMR spectrum

| 6.90-7.40 ppm | aromatic protons | 14H, m |
|---|---|---|
| 4.88 ppm | $CD_3\underline{O}D$ | s |
| 4.39 ppm | 5, 3 | 2H, m |
| 3.31 ppm | $C\underline{D_3}OD$ | m |
| 3.25 ppm | $\underline{7a}$ | 1H, m |
| 3.17 ppm | $(CH_3)_2\underline{CH}$ | 1H, m |
| 2.87 ppm | 7b | 1H, m |
| 2.54 ppm | 2 | 2H, d |
| 1.80-2.10 ppm | 6a, 4 | 3H, m |
| 1.40 ppm | 6b | 1H, m |
| 1.33 and 1.32 ppm | $(\underline{CH_3})_2CH$ | 6H, 2x d |
| $^{13}C$ NMR spectrum: | | |
| 180.5 ppm | 1 | |
| 165.5 ppm | $\underline{C}O-NH$ | |
| 164.4 ppm | $\underline{C}-F$ | d |
| 140.0-115.0 | aromatic carbons | |
| 97.2 ppm | 2' | |
| 94.9 ppm | 5' | |
| 74.4 ppm | 4' | |
| 70.6 ppm | 3' | |
| 70.4 ppm | 5 | |
| 69.3 ppm | 3 | |
| 49.1 ppm | $CD_3OD$ | m |
| 464. ppm | 2 | |
| 45.0 ppm | 4 | |
| 37.4 ppm | 7 | |
| 30.5 ppm | 6 | |
| 29.5 ppm | $(CH_3)_2\underline{CH}$ | |
| 19.5 and 18.3 ppm | $(\underline{CH_3})_2CH$ | |

Structural Elucidation of Compound ATV-Epoxy Furan:

Mass Spectrometry:

Conditions:

High-resolution mass spectra were obtained at the same conditions as those for compound ATV-cycloIP.

Adducts of molecular ion with sodium 472.1536 m/z and potassium 488.1270 are observed in mass spectrum. Calculated elemental composition in first case was $C_{26}H_{24}NO_5FNa$ (deviation between calculated and measured mass was 0.0 mDa), and in the second case $C_{26}H_{24}NO_5FK$ (deviation between calculated and measured mass was 0.5 mDa).

Protonated molecular ion was not observed due to fast elimination of water from molecule $(M+H-H_2O)^+=$ 432.1606 m/z. Proposed elemental composition was $C_{26}H_{23}NO_4F$. The deviation between calculated and measured mass was 0.5 mDa. That fragment ion also makes adducts with sodium and potassium.

An adduct of two molecules of compound ATV-epoxy furan and sodium is observed at 921.3131 m/z. Proposed elemental composition was $C_{52}H_{48}N_2O_{10}F_2Na$. Deviation between calculated and measured mass was 4.4 mDa.

Nuclear Magnetic Resonance spectroscopy:

Conditions:

$^1H$ and $^{13}C$ measurements were obtained in the same manner as for compound ATV-cycloIP.

| Solvent: | $CDCl_3$ ($^1H$ measurements) |
|---|---|
| | mixture of $CD_3OD:CDCl_3 = 2:1$ ($^{13}C$ measurements) |

15
-continued

Structure:

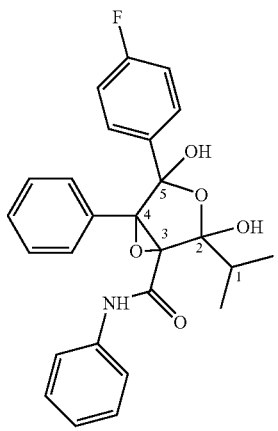

¹H NMR spectrum

| | | |
|---|---|---|
| 7.57 ppm | —NH | 1H, br |
| 6.90-7.50 ppm | aromatic protons | 14H, m |
| 6.05 ppm | —OH | 1H, br |
| 4.31 ppm | —OH | 1H, s |
| 2.38 ppm | (CH₃)₂CH | 1H, m |
| 1.22 and 1.21 ppm | (CH₃)₂CH | 6H, 2x d |

¹³C NMR spectrum:

| | | |
|---|---|---|
| 215.9 ppm | imp. | |
| 165.0 ppm | $\underline{C}$O—NH | |
| 164.0 ppm | $\underline{C}$—F | d |
| 140.0-115.0 ppm | aromatic carbons | |
| 107.1 ppm | 2 | |
| 104.1 ppm | 5 | |
| 77.0 ppm | CDCl₃ | t |
| 75.9 ppm | 4 | |
| 70.4 ppm | 3 | |
| 49.1 ppm | CD₃OD | m |
| 35.6 ppm | (CH₃)₂$\underline{C}$H | |
| 17.9 and 17.0 ppm | ($\underline{C}$H₃)₂CH | |

Structural Elucidation of Compound ATV-cycloFP:

Mass Spectrometry:

Conditions:

High-resolution mass spectra were obtained in the same manner as for the compound ATV-cycloIP.

Protonated molecular ion 591.2507 m/z was observed. The molecular ion is much less intensive in comparison to ATV-cycloIP. The most intensive ion in MS spectrum is 573.2406 m/z and it is formed with the elimination of water molecule.

The calculated elemental composition for 591.2507 m/z was $C_{33}H_{36}N_2O_7F$. The deviation between calculated and measured mass was 1.4 mDa. In comparison with atorvastatin the compound has two additional oxygen atoms in the structure.

Nuclear Magnetic Resonance Spectroscopy:

Conditions:

¹H and ¹³C measurements were obtained in the same manner as for compound ATV-cycloIP.

16

Solvent: CD₃OD (¹H and ¹³C measurements)

Structure:

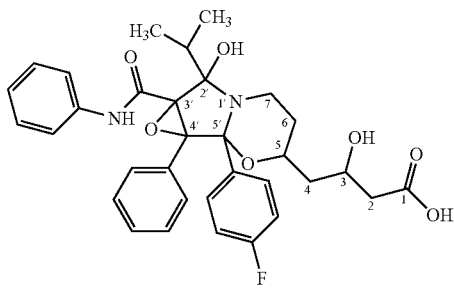

¹H NMR spectrum

| | | |
|---|---|---|
| 6.90-7.40 ppm | aromatic protons | 14H, m |
| 4.88 ppm | CD₃$\underline{O}$D | s |
| 4.13 ppm | 5 | 1H, m |
| 3.74 ppm | 3 | 1H, m |
| 3.36 ppm | 7a | 1H, m |
| 3.31 ppm | CD₃$\underline{O}$D | m |
| 2..97 ppm | 7b | 1H, m |
| 2.50 ppm | (CH₃)₂$\underline{C}$H | 1H, m |
| 2.37 and 2.27 ppm | 2 | 2H, 2xm |
| 2.07 ppm | 6a | 1H, m |
| 1.85 and 1.64 ppm | 4 | 2H, 2xm |
| 1.26 and 1.28 ppm | (CH₃)₂CH | 6H, 2xd |
| 1.25 ppm | 6b | 1H, m |

¹³C NMR spectrum

| | | |
|---|---|---|
| 180.2 ppm | 1 | |
| 167.1 ppm | $\underline{C}$O—NH | |
| 164.2 ppm | $\underline{C}$—F | d |
| 140.0-115.0 ppm | aromatic carbons | |
| 96.9 ppm | 2' | |
| 95.1 ppm | 5' | |
| 74.5 ppm | 4' | |
| 70.4 ppm | 5 | |
| 70.0 ppm | 3' | |
| 67.5 ppm | 3 | |
| 49.1 ppm | CD₃OD | m |
| 45.2 ppm | 2 | |
| 44.7 ppm | 4 | |
| 38.3 ppm | 7 | |
| 36.6 ppm | (CH₃)₂$\underline{C}$H | |
| 31.0 ppm | 6 | |
| 19.7 and 19.0 ppm | ($\underline{C}$H₃)₂CH | |

Structural Elucidation of Compound ATV-epoxy Dion:

Mass Spectrometry:

Conditions:

High-resolution mass spectra were obtained in the same manner as for the compound ATV-cycloIP.

Protonated molecular ion 432.1612 m/z was observed. The calculated elemental composition was $C_{26}H_{23}NO_4F$. The deviation between calculated and measured mass was 0.1 mDa.

MS/MS spectrum of protonated molecular ion is presented in Table 5.

TABLE 5

MS/MS spectra of protonated molecular ion 432 m/z - five most intensive peaks

| Mass | RA % | Calc. Mass | Error mDa | Error mDa | Formula |
|---|---|---|---|---|---|
| 226.0664 | 10.97 | 226.0668 | −0.4 | −1.8 | $C_{14}H_9NOF$ |
| 241.0659 | 11.86 | 241.0665 | −0.6 | −2.4 | $C_{15}H_{10}O_2F$ |
| 269.0603 | 10.67 | 269.0614 | −1.1 | −4.1 | $C_{15}H_{10}O_3F$ |
| 304.1138 | 100.00 | 304.1126 | −0.9 | −2.9 | $C_{20}H_{15}NOF$ |
| 344.1082 | 25.07 | 344.1087 | −0.5 | −1.4 | $C_{22}H_{15}NO_2F$ |
| 432.1611 | 16.08 | 432.1611 | 0 | 0 | $C_{26}H_{23}NO_4F$ |

Nuclear Magnetic Resonance Spectroscopy:
Conditions:
$^1$H and $^{13}$C measurements were obtained in the same manner as for the compound ATV-cycloIP.

Solvent: mixture of CD$_3$OD:CDCl$_3$ = 2:1 ($^1$H and $^{13}$C measurements)

Structure:

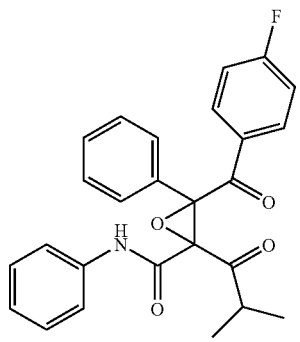

$^1$H NMR spectrum

| | | |
|---|---|---|
| 8.20-6.80 ppm | aromatic protons | 14H, m |
| 4.79 ppm | CD$_3$OD | s |
| 3.31 ppm | CD$_3$OD | m |
| 3.20 ppm | (CH$_3$)$_2$CH | 1H, m |
| 1.20 and 1.02 ppm | (CH$_3$)$_2$CH | 6H, 2x d |

$^{13}$C NMR spectrum:

| | | |
|---|---|---|
| 206.0 ppm | (CH$_3$)$_2$CH—CO— | |
| 191.4 ppm | phenyl-CO— | |
| 167.3 ppm | F—C | d |
| 162.8 ppm | CO—NH | |
| 140.0-115.0 ppm | aromatic carbons | |
| 77.0 ppm | CDCl$_3$ | t |
| 74.6 and 72.0 ppm | epoxy carbon atoms | |
| 49.0 ppm | CD$_3$OD | m |
| 38.3 ppm | (CH$_3$)$_2$CH | |
| 18.5 and 17.7 ppm | CH | |

EXAMPLE 2

Preparation and Isolation of ATV-cycloIP Compound 2 litres of atorvastatin solution was prepared in 80% acetonitrile and 20% water (vol/vol), containing 1 mg of atorvastatin per ml. The solution was put in a shallow crystallizer dish and was exposed to solar radiation for five hours. Immediately after that, the solution was alkalized with 1M solution of potassium hydroxide to pH 8 to 9 and evaporated under reduced pressure until the first occurrence of turbidity. The water bath temperature was kept under 30° C., and the condenser was cooled with water at 0° C.

The solution was then clarified with addition of a minimal amount of acetonitrile.

Preparative chromatography and structure elucidation was carried out in the same manner as in the example 1.

210 mg of pure ATV-cycloIP compound was isolated from the concentrated fraction by freeze drying. The chromatographic purity was 96.6%.

EXAMPLE 3

Preparation and Isolation of ATV-Epoxy Furan and ATV-Epoxy Dion Compounds 1 liter of atorvastatin solution was prepared in 80% acetonitrile/20% water (vol/vol)-containing 1 mg of atorvastatin per ml. The solution was put in a shallow crystallizing dish and was exposed to solar radiation for five hours. Immediately after the solution was acidified with 0.5M phosphoric acid to pH 3.0. The mixture was left at a room temperature for two hours and evaporated under reduced pressure to cca ⅓ of the original mixture volume.

Preparative chromatography and structure elucidations were carried out in the same manner as in the example 1.

120 mg of ATV-epoxy furan compound was isolated from the concentrated fraction by freeze-drying. The chromatographic purity was 92.6%.

21 mg of ATV-epoxy dion compound was isolated from the concentrated fraction by freeze-drying. The chromatographic purity was 95.1%.

EXAMPLE 4

Preparation and Isolation of ATV-cycloFP Compound 800 ml of solution of atorvastatin was prepared in acetonitrile, containing 10 mg of atorvastatin per ml. 4 ml of 12M sodium hydroxide and 40 ml of 30% hydrogen peroxide was added. The solution was stirred at 55° C. for five hours. The reaction mixture was allowed to cool and decanted. The supernatant was evaporated under reduced pressure to cca 50 ml. The remaining water was discarded and the solid residue washed with fresh water. The solid residue was then dissolved in acetonitrile.

Preparative chromatography and structure elucidation was carried out in the same manner as in example 1

230 mg of pure ATV-cycloIP compound was isolated from the concentrated fraction by freeze-drying. The chromatographic purity was 98.3%.

EXAMPLE 5

Atorvastatin calcium can be prepared by any way described in the literature. The only requirement during the whole process of the preparation of atorvastatin calcium was that the inert atmosphere must be maintained. The content of the each oxidative degradation product ATV-cycloIP, ATV-epoxy furan, ATV-cycloFP and ATV-epoxy dion compounds using HPLC method and detection at 250 nm in so prepared atorvastatin calcium were below 0.04%.

EXAMPLE 6

The atorvastatin calcium obtained by procedure described in example 1 was stored under nitrogen atmosphere at the room temperature for 2 years. The content of each oxidative degradation product ATV-cycloIP, ATV-epoxy furan, ATV-cycloFP and ATV-epoxy dion compounds using HPLC method and detection at 250 nm in so prepared atorvastatin calcium were below 0.1%.

EXAMPLE 7

The atorvastatin calcium obtained by procedure described in example 1 was stored under air at room temperature for 2 years. The content of the oxidative degradation product ATV-cycloIP, ATV-epoxy furan, ATV-cycloFP and ATV-epoxy dion compounds using HPLC method and detection at 250 nm in so prepared atorvastatin calcium were 0.856%, 0.636%, 0.905% and 0.741%, respectively.

EXAMPLE 8

Tablets were prepared using atorvastatin calcium obtained by procedure described in example 1 and at least one pharmaceutically acceptable excipient. In the so prepared tablets the content of the oxidative degradation product ATV-cycloIP, ATV-epoxy furan, ATV-cycloFP and ATV-epoxy dion compounds using HPLC method and detection at 250 nm were 0.11%, 0.07%, 0.07% and 0.08%, respectively.

Tablets were packed in alu/alu blisters in the nitrogen atmosphere. Blisters were stored at the room temperature for two years. The content of oxidative degradation product ATV-cycloIP, ATV-epoxy furan, ATV-cycloFP and ATV-epoxy dion compounds using HPLC method and detection at 250 nm were 0.18%, 0.08%, 0.17% and 0.09%, respectively.

EXAMPLE 9

Tablets as described in Example 8 were packed in alu/alu blisters in air. In the so prepared tablets the content of the oxidative degradation product ATV-cycloIP, ATV-epoxy furan, ATV-cycloFP and ATV-epoxy dion compounds, using HPLC method and detection at 250 nm were 0.13%, 0.09%, 0.08% and 0.08%, respectively.

Blisters were stored at the room temperature for two years. The content of oxidative degradation product ATV-cycloIP, ATV-epoxy furan, ATV-cycloFP and ATV-epoxy dion compounds using HPLC method and detection at 250 nm in so prepared atorvastatin calcium were 1.75%, 0.61%, 1.23% and 0.65% respectively.

The invention claimed is:
1. A process for the preparation of a compound 4-[6-(4-fluoro-phenyl)-6-hydroxy-1b-isopropyl-6a-phenyl-1a-phenylcarbamoyl-hexahydro-1,2-dioxa-5 a-aza-cyclopropa[a]inden-3-yl]-3-(R)hydroxy-butyric acid or 4-[1b-(4-fluoro-phenyl)-6-hydroxy-6-isopropyl-1a-phenyl-6a-phenylcarbamoyl-hexahydro-1,2-dioxa-5 a-azacyclopropa[a]inden-3-yl]-3-(R)-hydroxy-butyric acid characterized in that a solid atorvastatin salt is oxidized in an air or oxygen atmosphere at an elevated temperature from 40 to 90° C.

2. The process according to claim 1 wherein the solid atorvastatin salt is selected from the group consisting of atorvastatin calcium, sodium, potassium, magnesium and ammonium.

3. The process according to claim 1 wherein the oxidation of atorvastatin salt is performed in a solution of an atorvastatin salt in water and/or organic solvent and/or mixtures of solvents selected from the group consisting of acetonitrile, methanol, ethanol, propanol, dichloromethane or methylene chloride, with the addition of hydrogen peroxide or by blowing air or oxygen through the solution at a temperature of about 40 to 90° C.

* * * * *